United States Patent [19]

Friederang et al.

[11] 4,146,724

[45] Mar. 27, 1979

[54] PROCESS FOR THE MANUFACTURE OF ISOPROPYL 4-METHYLIMIDAZOLE-5-CARBOXYLATE

[75] Inventors: Albrecht Friederang; Horst Koenig, both of Ludwigshafen, Fed. Rep. of Germany

[73] Assignee: BASF Aktiengesellschaft, Rheinland, Fed. Rep. of Germany

[21] Appl. No.: 836,060

[22] Filed: Sep. 23, 1977

[30] Foreign Application Priority Data

Dec. 24, 1975 [DE] Fed. Rep. of Germany ..... 25,585,175

Related U.S. Application Data

[62] Division of Ser. No. 737,722, Nov. 1, 1976, abandoned.

[51] Int. Cl.$^2$ ............................................ C07D 233/90
[52] U.S. Cl. ............................................ 548/343
[58] Field of Search ..................... 548/343; 560/178

[56] References Cited

U.S. PATENT DOCUMENTS

| | | | |
|---|---|---|---|
| 2,228,452 | 1/1941 | Gleason | 560/178 |
| 3,549,693 | 12/1970 | Eck et al. | 560/178 |

FOREIGN PATENT DOCUMENTS

| | | | |
|---|---|---|---|
| 9036138 | 8/1962 | United Kingdom | 560/178 |
| 994640 | 6/1965 | United Kingdom | 560/178 |
| 1175240 | 12/1969 | United Kingdom | 560/178 |

OTHER PUBLICATIONS

Bredereck et al., I. Chem. Berichte, 1953, vol. 86, pp. 88–96.
Bredereck et al., II Chem. Berichte, 1960, vol. 93, pp. 2083–2084.
Bredereck et al., III In: Foerst Newer Methods of Preparative Organic Chemistry, vol. 3, pp. 256–261, N.Y., Academic Press, 1964.
Gaudry et al., Bull. Soc. Chim. France, 1967, pp. 1849–1850.
Grimmett, In: Katritzky et al., Advances in Heterocyclic Chemistry, vol. 12, pp. 113-115, N.Y., Academic Press, 1970.
Organic Syntheses I, 1953, vol. 33, pp. 45–46.
Organic Syntheses II, 1962, vol. 42, p. 28.
Schubert et al., I, Chem. Abst., 1968, vol. 68, No. 49508q.
Schubert et al. II, Chem. Abst., 1960, vol. 54, col. 7694.
Bohme et al., I, Chem. Berichte, 1958, vol. 91, pp. 988–996.
Bohme et al., II, Chem. Abst., 1960, vol. 54, cols. 1284–1285.

*Primary Examiner*—Natalie Trousof
*Attorney, Agent, or Firm*—Keil & Witherspoon

[57] ABSTRACT

The new isopropyl 4-methylimidazole-5-carboxylate and a new process for its manufacture by reacting isopropyl chloroacetoacetate with formamide and water in the presence of formic acid. Isopropyl 4-methylimidazole-5-carboxylate, manufactured by the process of the invention, is a starting material for the manufacture of dyes, pharmaceuticals and pesticides.

9 Claims, No Drawings

PROCESS FOR THE MANUFACTURE OF ISOPROPYL 4-METHYLIMIDAZOLE-5-CARBOXYLATE

This is a division of application Ser. No. 737,722, filed Nov. 1, 1976, now abandoned.

The present invention relates to the new isopropyl-4-methylimidazole-5-carboxylate and to a process for its manufacture by reacting isopropyl chloroacetoacetate with formamide and water in the presence of formic acid.

Chemische Berichte, 91 (1958), 989 and 993, discloses that ethyl α-chloroacetoacetate can be reacted with formamide and water at 150° C. to give ethyl 4-methylimidazole-5-carboxylate in a yield of 32 percent of theory. Water is added in a molar ratio of 2:1, based on the ester starting material. The above publication also discloses that if the reaction is carried out in the absence of water, with ethyl α-hydroxyacetoacetate as the starting material, the yield is only 12 percent of theory. In both cases, working up is complicated; formamide must be distilled off and the residue must then be left to stand for several days in a refrigerator in order to crystallize. The process gives an unsatisfactory yield of end product and does not permit simple and economical operation, and is described in the said publication for the manufacture of the ethyl ester only.

It is an object of the present invention to provide a new process whereby isopropyl 4-methylimidazole-5-carboxylate can be manufactured in far better yield and purity.

A further object of the present invention is to provide the new isopropyl 4-methylimidazole-5-carboxylate.

We have found that these objects are achieved and that isopropyl 4-methylimidazole-5-carboxylate is advantageously obtained by reacting chloroacetoacetic acid esters with formamide and water at elevated temperatures if the reaction is carried out with isopropyl chloroacetoacetate in the presence of formic acid.

Further, we have found that the new isopropyl 4-methylimidazole-5-carboxylate is obtained.

The reaction can be represented by the following equation:

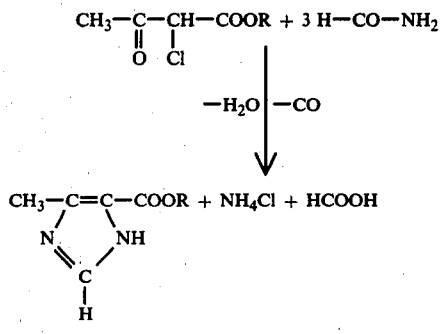

In comparison to the conventional processes using the ethyl ester as the starting material, the process of the invention, surprisingly, gives isopropyl 4-methylimidazole-5-carboxylate in far better yield and purity. The end product can be isolated more simply and more rapidly from the reaction mixture. Problems of effluent pollution and of product purification are reduced and the process causes less environmental pollution. All these advantageous results of the process of the invention are surprising in the light of the prior art. It was not to be expected that in the presence of formic acid the reaction according to the invention would give far better yields of end product even if the amounts of water added are less, or no water is added at all.

Isopropyl chloroacetoacetate is reacted with formamide in the stoichiometric amount or in excess, preferably in a ratio of from 3 to 15 moles of formamide per mole of isopropyl chloroacetoacetate. Preferably, the reaction is carried out with a ratio of from 0.5 to 10, especially from 1 to 3, moles of formic acid per mole of isopropyl chloroacetoacetate. In general, the reaction is carried out at from 50° to 200° C., preferably from 70° to 180° C., especially from 100° to 170° C., under atmospheric or superatmospheric pressure, continuously or batchwise, and advantageously without adding water or with from 0.5 to 10 moles, advantageously from 0.5 to 1.9 moles, and especially from 1 to 1.55 moles, of water per mole of isopropyl chloroacetoacetate. If desired, organic solvents which are inert under the reaction conditions, for example aromatic hydrocarbons, e.g. xylene, benzene, toluene, nitrobenzene, chlorobenzene or dichlorobenzene, are used; suitable amounts of organic solvent are from 5 to 50 percent by weight, based on isopropyl chloroacetoacetate.

The reaction may be carried out as follows: a mixture of isopropyl chloroacetoacetate, formamide, formic acid and, advantageously, water, is kept at the reaction temperature for from 1 to 6 hours. The end product is then isolated in the usual manner, for example by fractional distillation, cooling the residue for from 1 to 12 hours, filtering off the end product and, if appropriate, washing it with water and filtering it off again.

In a preferred embodiment, the starting material isopropyl chloroacetoacetate is first manufactured, for example by reacting diketene and isopropenol in accordance with the method described, in Organic Syntheses, 42 (1962), 28, for the manufacture of the tert.-butyl ester, followed by chlorination in accordance with the method described for the manufacture of ethyl chloroacetoacetate in Organic Syntheses, 33 (1953), 45. The resulting reaction mixture from the chlorination is heated and dissolved reaction gases are advantageously removed under reduced pressure. Formamide, water, formic acid and, if appropriate, an organic solvent are added and the reaction according to the invention is carried out in the manner described above.

Isopropyl 4-methylimidazole-5-carboxylate, manufactured by the process of the invention, is a valuable starting material for the manufacture of dyes, pharmaceuticals and pesticides. For example, the reaction of isopropyl 4-methylimidazole-5-carboxylate with lithium aluminum hydride can be used to manufacture 4-methyl-5-(hydroxymethyl)-imidazole, which can be converted into aminomethyl-imidazole (British Pat. No. 1,341,375), which resembles histamine.

Starting from 4-methyl-5-(hydroxymethyl)-imidazole, it is also possible to obtain new N-cyanoguanidine derivatives and thiourea derivatives (Belgian Pat. Nos. 832,660, 832,662, 832,663, 832,664 and 832,665) which may be used as histamine antagonists and drugs for the treatment of gastric secretion disorders.

In the Examples which follow, parts are by weight.

EXAMPLE 1

71.5 parts of crude, 93 percent by weight pure, isopropyl chloroacetoacetate (manufactured by chlorinating 58 parts of isopropyl acetoacetate with 62 parts of sulfuryl chloride at 0° – 5° C. for 4 hours and removing excess residual gases, in the form of hydrogen chloride and sulfur dioxide, at 40° C. and 20 mm Hg) are stirred with 180 parts of formamide, 40 parts of formic acid and 10 parts of water for 5 hours at 145° C. The mixture is concentrated and the residue (250 parts) is kept at 0° – 5° C. for 10 hours. The mixture is filtered and the solid product is stirred for one hour with 100 parts of water, filtered off and dried. 35 parts (56 percent of theory) of isopropyl 4-methylimidazole-5-carboxylate of melting point 188° – 190° C. are obtained.

EXAMPLE 2

The reaction is carried out as described in Example 1, but without adding water. 29 parts of isopropyl 4-methylimidazole-5-carboxylate (46 percent of theory), of melting point 188° – 190° C., are obtained.

EXAMPLE 3

The reaction is carried out as described in Example 1 with 60 parts of formic acid. 34 parts of isopropyl 4-methylimidazole-5-carboxylate (54 percent of theory), of melting point 187° – 189° C., are obtained.

We claim:
1. A process for the manufacture of isopropyl 4-methylimidazole-5-carboxylate which comprises reacting at an elevated temperature of from 50° to 200° C.
   (a) isopropyl chloroacetoacetate with
   (b) water in an amount up to about 10 moles of water per mole of isopropyl chloroacetoacetate, and
   (c) a stoichiometric amount or an excess of formamide, in the presence of
   (d) formic acid in a ratio of from 0.5 to 10 moles of formic acid per mole of isopropyl chloroacetoacetate.

2. A process as claimed in claim 1, wherein the reaction is carried out using a ratio of from 3 to 15 moles of formamide per mole of isopropyl chloroacetoacetate.

3. A process as claimed in claim 1, wherein the reaction is carried out at from 70° to 180° C.

4. A process as claimed in claim 1, wherein the reaction is carried out at from 100° to 170° C.

5. A process as claimed in claim 1, wherein the reaction is carried out without adding water.

6. A process as claimed in claim 1, wherein the reaction is carried out with from 0.5 to 10 moles of water per mole of isopropyl chloroacetoacetate.

7. A process as claimed in claim 1, wherein the reaction is carried out with from 0.5 to 1.9 moles of water per mole of isopropyl chloroacetoacetate.

8. A process as claimed in claim 1, wherein the reaction is carried out with from 1 to 1.55 moles of water per mole of isopropyl chloroacetoacetate.

9. A process as claimed in claim 1, wherein isopropyl chloroacetoacetate is first manufactured by reacting diketene and isopropenol, followed by chlorination, and the resulting reaction mixture from the chlorination is heated, dissolved reaction gases are removed under reduced pressure, formamide, water, formic acid and, if appropriate, an organic solvent are added, and the reaction is carried out.

* * * * *